United States Patent [19]

Kukolja

[11] 3,962,276
[45] June 8, 1976

[54] AZETIDINONE ACETIC ACID INTERMEDIATES FOR 5-EPI-PENICILLINS

[75] Inventor: Stjepan Kukolja, Indianapolis, Ind.

[73] Assignee: Eli Lilly and Company, Indianapolis, Ind.

[22] Filed: Nov. 14, 1974

[21] Appl. No.: 523,766

Related U.S. Application Data

[60] Division of Ser. No. 165,758, July 15, 1971, Pat. No. 3,897,445, which is a continuation-in-part of Ser. No. 148,129, May 28, 1971, abandoned.

[52] U.S. Cl............................ 260/326 S; 260/239 A; 260/239.3 R; 260/281 GN; 260/307 H; 260/326 E; 260/326.37
[51] Int. Cl.²................ C07D 403/04; C07D 205/08
[58] Field of Search ....... 260/239 A, 326 S, 326.37, 260/307 H, 239.3 R, 281 GN, 326.5 FM, 326 E, 281 N

[56] References Cited
UNITED STATES PATENTS 3,840,556   10/1974   Kukolja............................ 260/239 A

*Primary Examiner*—Alton D. Rollins
*Assistant Examiner*—Mark L. Berch
*Attorney, Agent, or Firm*—William C. Martens, Jr.; Everet F. Smith

[57] ABSTRACT

5-Epi-penicillin esters and acids, the acids being useful as inhibitors of β-lactamase type enzymes, a process for preparing such compounds by reacting an ester of a 2-halo-α-(1'-halothio-1'-methylethyl)-4-oxo-3-imido-1-azetidineacetate with (*a*) zinc in acid or (*b*) stannous chloride in an organic liquid medium at 0° to 100°C., and some new 2-halo-α-(1'-cyanodithia- or 1'-mercapto-1'-methylethyl)-4-oxo-3-imido-2-azetidineacetate which are useful as intermediates in preparing the 5-epi-penicillins.

5 Claims, No Drawings

AZETIDINONE ACETIC ACID INTERMEDIATES FOR 5-EPI-PENICILLINS

CROSS REFERENCE

This is a division, of application Ser. No. 165,758, filed July 15, 1971, now U.S. Pat. No. 3,897,445, which is a continuation-in-part of my application Ser. No. 148,129, filed May 28, 1971, now abandoned.

INTRODUCTION

This invention relates to penicillin compounds having a new steric configuration, and to processes for preparing them. More particularly, this invention provides some new 5-epi-penicillin esters and acids which acids are useful as inhibitors of β-lactamase enzymes, a process for preparing such 5-epi-penicillins, and some new 2-halo-α-(1'-cyanodithio- or 1'-mercapto-1'-methylethyl)-4-oxo-3-imido-2-azetidineacetates which are useful as intermediates in the preparation of the 5-epi-penicillin compounds of this invention.

BACKGROUND OF THE INVENTION

In my prior co-pending application Ser. No. 148,129, filed May 28, 1871, I described and claimed some new 2-halo-α-(1'-sulfenylhalo-1'-methylethyl)-4-oxo-1-azetidineacetate ester and acid compounds of the formula

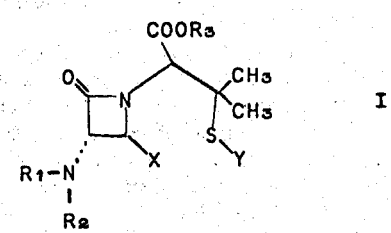

wherein $R_1$ is an acyl group and $R_2$ is hydrogen, or $R_1$ and $R_2$ taken together with the nitrogen to which they are bonded define a phthalimido or succinimido group; $R_3$ is hydrogen or $C_1$ to $C_4$-alkyl, trichloroethyl, benzyl, p-nitrobenzyl, p-methoxybenzyl, benzhydryl, phthalimido or phenacyl, X is chloro, bromo or $C_2$ to $C_6$-alkanoyloxy, and Y is chloro, bromo, N-benzotriazolyl, or succinimido. Those compounds are prepared by selectively opening the $S_1$-$C_5$-bond of the thiazolidine ring of a 6-acylamido or a 6-imidopenicillin ester by reacting the penicillin ester with an electrophilic reagent in the form of a source of positive halogen in an aprotic solvent.

SUMMARY OF THE INVENTION

This invention provides new 5-epi-penicillin esters and acids. The acids are useful as inhibitors of β-lactamase enzymes e.g. in fermentation media. The new 5-epi-penicillins are prepared by reacting a 2-halo-α-(1'-halothio, mercapto, or -SSCN-1'-methylethyl)-4-oxo-3-imido-1-azetidineacetate ester with (a) zinc in acid or (b) stannous chloride in an organic liquid medium at 0° to 100°C. The 5-epi-penicillin acids are prepared from the esters by deesterification with acid or by hydrogenation procedures. This invention also provides some new 2-halo-α-(1'-cyanodithio- or 1'-mercapto-1'-methylethyl)-4-oxo-3-imido-1-azetidineacetate esters and acids which are useful as intermediates in preparing the new 5-epi-penicillins of this invention.

DETAILED DESCRIPTION OF THE INVENTION

One aspect of this invention provides new 5-epi-penicillin esters and acids of the formula

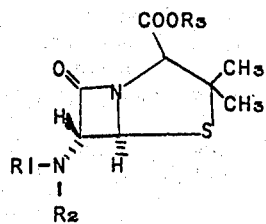

wherein $R_1$, taken alone, denotes an acyl group of the formula $$R_a—CH_2—CO—$$

wherein $R_a$ is

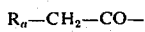

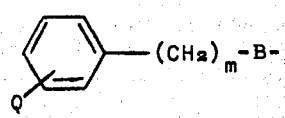

Q is hydrogen, chloro, bromo, $C_1$–$C_3$ alkyl, $C_1$–$C_3$ alkoxy, nitro or cyano;
B is oxygen, or a carbon to carbon bond; and
m is an integer of 0 to 2;
$R_2$, taken alone, is defined as $R_1$ above, or is

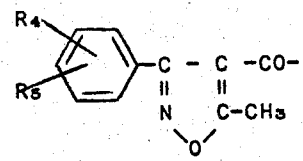

where each of $R_4$ and $R_5$ is hydrogen or halogen (fluorine, chlorine, bromine, or iodine); $R_1$ and $R_2$ are taken together with the nitrogen to which they are bonded to form a cyclic imide group or radical having from 3 to about 20 carbon atoms, and $R_3$ is hydrogen or the residue of an ester group which is removable by acid or hydrogenation procedures. A preferred sub-group of these new compounds are those wherein $R_1$ and $R_2$ are taken together with the nitrogen to which they are bonded to form a succinimido or phthalimido group or bis acylimide group and $R_3$ is hydrogen or a $C_1$ to $C_4$-alkyl, p-nitrobenzyl, p-methoxybenzyl, benzyl, benzhydryl, phthalimidomethyl, succinimidomethyl, 2,2,2-trichloroethyl, trimethylsilyl, phenacyl, or p-halophenacyl where halo denotes chlorine or bromine.

Examples of compounds of this invention include:

p-Nitrobenzyl 6-[N-(phenoxyacetyl)phenylacetamido]-5-epi-pencillanate
Benzhydryl 6-[N-(3',4'-dichlorophenylacetyl)phenoxyacetamido]-5-epi-penicillanate
tert-Butyl 6-[N-(4'-methoxyphenylacetyl)phenoxyacetamido]-5-epi-penicillanate
p-Methoxybenzyl 6-[N-(3'-methylphenylacetyl)phenylpropionamido]-5-epi-penicillanate, Phthalimidomethyl 6-[N-(4'-nitrophenoxyacetyl)-phenoxyacetamido]-5-epi-penicillanate,
Succinimidomethyl 6-[N-(3'-cyanophenylacetyl)-phenylacetamido]-5-epi-penicillanate,
2,2,2-Trichloroethyl 6-diglycolimido-5-epi-penicillanate,
p-Nitrobenzyl 6-[N-(phenoxyacetyl)-phenylacetamido]-5-epi-penicillanate,
Benzhydryl 6-3-nitrophthalimido-5-epi-penicillanate,
tert-Butyl 6-phthalimido-5-epi-penicillanate,
2,2,2-Trichloroethyl 6-succinimido-5-epi-penicillanate,
Benzyl 6-bisphenylacetylimido-5-epi-penicillanate,
p-Nitrobenzyl 6-(methylmalonimido)-5-epi-penicillanate,
Phenacyl 6-glutarimido-5-epi-penicillanate,
2,2,2-Trichloroethyl N-(3'-phenyl-5'-methyl-4-isoxazolyl)-phenylacetylamido-5-epi-penicillanate,
p-Methoxybenzyl 6-(4'-chlorophthalimido)-5-epi-penicillanate,
Phthalimidomethyl 6-succinimido-5-epi-penicillanate,
Methyl 6-diglycolimido-5-epi-penicillanate,
Benzhydryl 6-phthalimido-5-epi-penicillanate, and the corresponding acids, which are obtained after deesterification by treatment of the esters with acids such as trifluoroacetic acid, hydrochloric acid, zinc in formic, acetic, or hydrochloric acid, or by hydrogenating the ester with hydrogen in the presence of a palladium or rhodium metal or compound, in suspension or on a carrier such as barium sulfate, carbon, alumina or the like.

The configuration of these new 5-epi-penicillin compounds can be compared to that of natural penicillins by the formulas III and IV which follow depicting the trans-arrangement of protons in the azetidinone ring, and consequently the trans or 5-epi-fusion of the azetidinone and thiazolidine rings of a 5-epi-penicillin in formula III

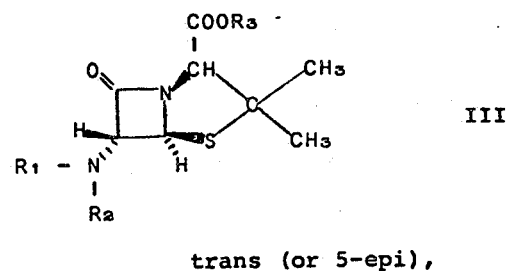

trans (or 5-epi), wherein $R_1$, $R_2$ and $R_3$ are as defined above, and wherein the 4-membered azetidinone ring is considered as being on a plane with the paper surface and the thiazolidine ring angles up. In the case of the natural penicillin configuration, when the azetidinone ring is considered as being on a plane with the paper surface the thiazolidine ring angles down, resulting in the cis-arrangement of β-lactam protons shown by formula IV

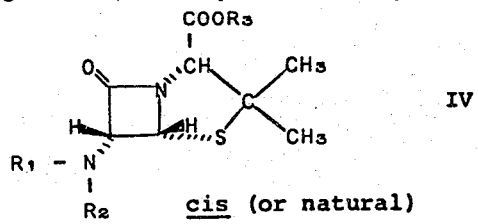

cis (or natural)

The cyclic imide group or radial defined by $R_1$ and $R_2$ being taken together with the nitrogen to which they are bonded can be formed by reacting the 6-amino group of 6-aminopenicillanic acid (6-APA) or a 6-aminopenicillin ester with a $C_3$ to $C_{20}$-hydrocarbon dibasic acid or an anhydride or other reactive variant thereof, followed by reacting the resulting derivative with a $C_1$ to $C_4$-alkyl haloformate, e.g., ethyl chloroformate, in the presence of an organic base. Cyclic imides can be made from succinic, glutaric, diglycolic, phthalic acids or anhydrides, as well as from cyclohexanedicarboxylic, 3-cyclohexene-1,2-dicarboxylic, halogen substituted dicarboxylic acids or anhydrides such as 4,5-dichlorophthalic, tetraiodophthalic, p-bromophthalic, as well as related epoxy bridged compounds such as 2,5-epoxycyclohexane-1,2-dicarboxylic, and 2,5-epoxy-3-cyclohexene-1,2-dicarboxylic acids and anhydrides, and compounds of similar reactivites to form cyclic imides. Additional examples of cyclic anhydrides of the type defined are found in the prior art such as in the *Journal of Organic Chemistry*, Volume 26, pp. 3365–3367 (September, 1961). 6-Phthalimido penicillanic acid was prepared starting with 6-APA and N-carboethoxyphthalimide according to the procedure of Y. G. Perron et al., *Journal of Medicinal Chemistry* Vol. 5, (1962), p 1016.

The acyclic imide group or radical defined by $R_1$ and $R_2$ being acyl groups can be formed by reacting the imidoyl chloride of penicillin esters (V) with an alkali metal salts (sodium and potassium being the most practical) of acids as described in the prior art such as in Netherlands Pat. No. 7,005,198 and Belgian Pat. No. 738,110. These reactions can be illustrated with the following formulas:

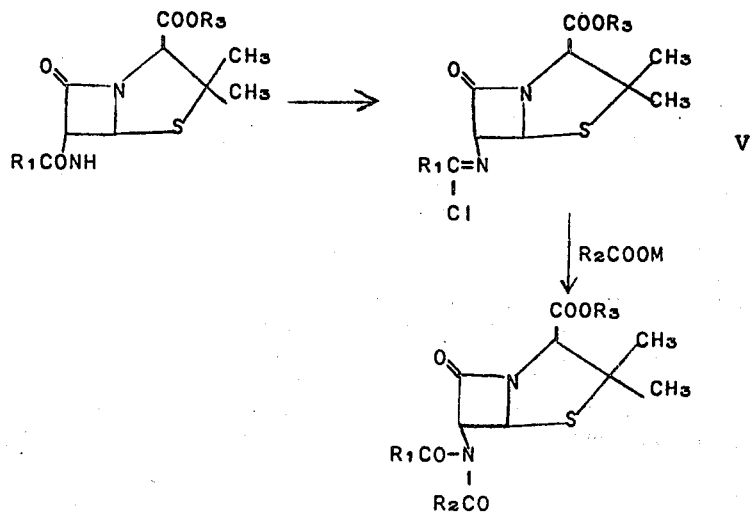

The new 5-epi-penicillin esters are useful as intermediates for preparing compounds where $R_3$ is hydrogen, or a salt thereof. The most common salt would be sodium, potassium, ammonium, tris($C_1$ to 4-alkyl)amine salts. The new 5-epi-penicillin acids are useful as inhibitors of β-lactamase type enzymes in fermentation media. For example, the compound 6-phthalimido-5-epi-penicillanic acid was found to inhibit over one-half of the cephalosporinase enzyme in an agar plate test in which the bioactivity of cephalosporin C against Salmonella sp. was measured. Similar inhibition of β-lactamase was found by bioassay methods using cephaloridine as the antibiotic and B. subtilis, K. pneumoniae and Mycobacterium avium as the test microorganisms.

According to the process of this invention the new 5-epi-penicillin ester or acid III is prepared by treating or reacting a compound of formula I reagents such as anhydrous stannous chloride. Without intending to limit the process of this invention to the mechanism of reaction, I believe that the reaction causes the formation of a transient intermediate of the structure

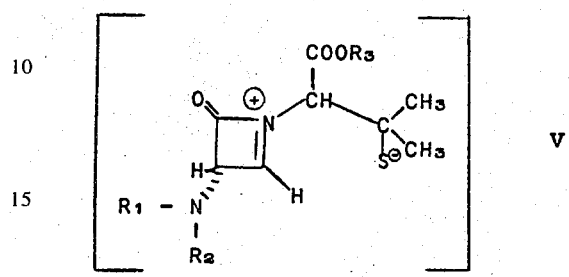

V

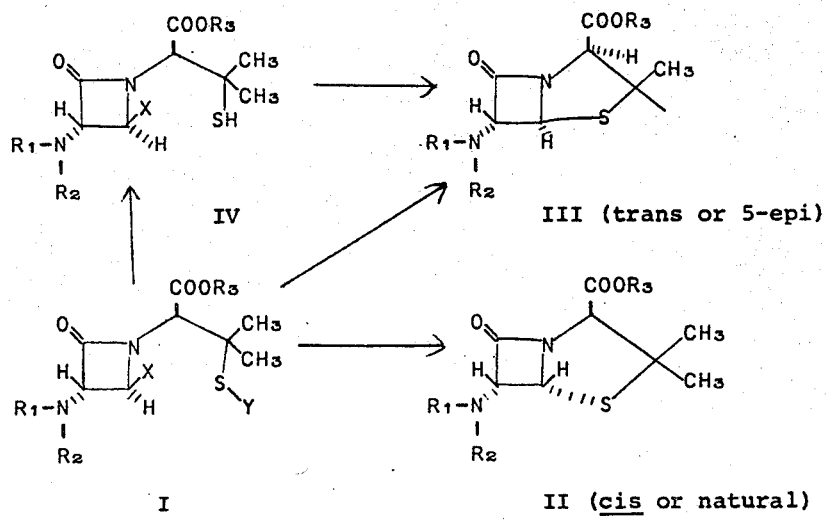

wherein $R_1$, $R_2$, and $R_3$ defined above, X is chlorine or bromine, and Y is chlorine, bromine, hydrogen or —SCN, with a member of the group consisting of (a) zinc in an acid medium, (b) stannous chloride in a liquid organic medium at a temperature of from about 0° to about 100°C., or (c) the compound IV can also be cyclized to 5-epi-penicillin (III) with zinc chloride in place of the stannous chloride. In aprotic solvents and using anhydrous reagents and conditions the reaction mixture product will be substantially (over 90 percent) the 5-epi-penicillin configuration (III). However, as the polarity of the solvent or reaction mixture is increased the yield or percentage of the cis (natural) penicillin (II) [and the 1'-mercapto intermediate (IV)] is correspondingly enhanced. Thus this invention provides a method for obtaining substantially the 5-epi-penicillin (III), if that is the desired product, in which case one would use an aprotic solvent and anhydrous cyclization which intermediate cyclizes to a mixture of the cis- and trans-isomers of the imido penicillin ester or acid, the proportions of each depending upon the protic state of the reaction medium.

The 2-halo-α-(1'-halothio-1-methylethyl)-4-oxo-3-imido-1-azetidineacetate ester starting materials can be prepared by treating a 6-imido-penicillanate ester with an electrophilic reagent which serves as a source of positive halogen to effect selective cleavage or opening of the thiazolidine ring between the $S_1$ and the carbon atom in the 5-position of the penicillin. The electrophilic cleavage of the thiazolidine ring results in the formation of a mixture of cis- and trans-isomers of the hydrogen on the 2-carbon atom of the resulting 2-azetidinone ring of the azetidine acetate.

The electrophilic reagent is preferably formed of an electrophilic component X, a source of positive halogen, and a nucleophilic component Y. As used herein, the term "source of positive halogen" is intended to refer to and include any source of $X_1^+$, wherein $X_1$ is chlorine or bromine. A wide variety of halogenating agents are known to those skilled in the art as supplying positive halogen and can be used to prepare the starting materials. Examples of halogenating agents which can be used include the elemental halogens such as chlorine and bromine, sulfuryl chloride, sulfuryl bromide, N-halogeno amides and imides such as N-chlorosuccinimide, N-bromosuccinimide, N,N-dibromohydantoins, and organic hypohalide and particularly the alkanoyl hypohalides such as acetyl hypochlorite, butyryl hypochlorite, acetyl hypobromite, propionyl hypobromite, butyryl hypobromite, and the like. In addition, use can be made of mixed halogens such as BrCl, ClI, BrI, and the like. As can be appreciated by those skilled in the art, the use of such mixed halogens provides a product containing mixed halogens. The reaction between the penicillin ester and the electrophilic reagent is preferably carried out in an aprotic solvent such as tetrahydrofuran, dioxane, aliphatic and aromatic hydrocarbons and halogenated hydrocarbons such as benzene, toluene, dichlorobenzene, methylene chloride, chloroform, bromoform, carbon tetrachloride, carbon tetrabromide and the like. The temperature of this reaction can vary over a wide range depending upon the nature of the side chain of the penicillin starting material. With 6-bis(acyl)-imido side chains temperatures of from −76°C. to 0°C., and with 6-cycloimido side chains the temperature can vary from −76°C. to 80°C.

The cyclization reaction of the process of this invention favors the formation of the 5-epi-penicillin when an aprotic solvent such as tetrahydrofuran or dioxane and anhydrous conditions are used. Examples of aprotic solvents which can be used are given above where the description of the preparation of the starting materials is given. The ratio of the natural penicillin configuration in the product increases as the protic condition of the reaction mixture is increased. These conditions are enhanced by small amounts of water introduced with reactants or solvents.

As part of this invention new compounds of the formula

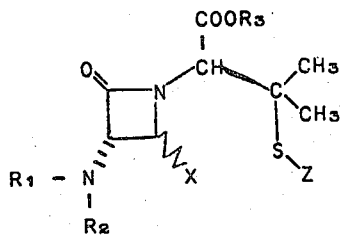

wherein $R_1$ and $R_2$ and $R_3$ are as defined above, X is chlorine or bromine and Z is hydrogen or —SCN can be made and used as reactants in preparing the 5-epi-penicillin compounds of this invention. The compound where Z is hydrogen is obtained when the 2-halo-α-(1′-halothio-1′-methylethyl)-4-oxo-3-imido-1-azetidineacetate ester, where halo is chloro or bromo, is treated with a hydrated stannous chloride or reduced with an alkali metal, (sodium and potassium being the most practical examples) or ammonium iodide in an aprotic organic liquid medium such as in tetrahydrofuran at room temperature for about 2 hours. This product (IV) can then be cyclized to the 5-epi-penicillin compound of this invention with anhydrous stannous or zinc chloride.

The 2-halo-α-(1′-cyanodithio-1′-methylethyl)-4-oxo-3-imido-1-azetidineacetate compounds (where Z is -SCN) are obtained by reacting an alkali metal thiocyanate such as sodium or potassium thiocyanate with the 2-halo-α-(1′-halothio-1′-methylethyl)-4-oxo-3-imido-1-azetidineacetate in an aprotic solvent at 0° to 50°C., preferably at room temperature. These cyanodithio compounds can be used in the process for preparing the 5-epi-penicillins of this invention as described above.

The invention is further illustrated by the following detailed examples, which are not intended to be limiting of the scope of the invention.

EXAMPLE 1

Preparation of Methyl 6-phthalimido-5-epi-penicillanate

A mixture of 3.6 g. of trans methyl 2-chloro-α-(1′-chlorothio-1′-methylethyl)-4-oxo-3-phthalimido-1-azetidineacetate and 2.5 g. of stannous chloride dihydrate and 100 ml. of dioxane was heated on a steam bath for 1 hour. The residue obtained after evaporation of the solvent was dissolved in chloroform, the solution washed twice with water and dried. The crude product, 2.2 g., was a mixture of trans (5-epi) and cis penicillins in a ratio of about 5:1 trans:cis. It was recrystallized from methyl ethyl ketone-cyclohexane; 670 mg. of colorless prisms of methyl 6-phthalimido-5-epi-penicillanate were collected. A second crop gave 420 mg. Analytical sample melted at 174°–175°C.; $[\alpha]_D$−192° (CHCl$_3$); nmr (CDCl$_3$) 90 (s, 3H), 102 (s, 3H), 231 (s, 3H), 234 (s, 1H), 327 (d, 1H, J = 2.0 Hz), 334 (d, 1H) J = 2.0 Hz), and 471 cps (m, 4 ArH); ir (CHCl$_3$) 1795 (α-lactam CO); 1785 and 1733 (phthalimido CO), and 1752 cm$^{-1}$ (ester CO).

Anal. calc. for $C_{17}H_{16}N_2O_5S$: C, 56.67; H, 4.47; N, 7.78; O, 22.20; S, 8.90. Found: C, 56.68; H, 4.60; N, 8.02; O, 21.92; S, 9.05%.

EXAMPLE 2

Preparation of 2,2,2-Trichloroethyl 6-phthalimido-5-epi-penicillanate

A mixture of 2.74 g. of 2,2,2-trichloroethyl 2-chloro-α-(1′-chlorothio-1-methylethyl)-4-oxo-3-phthalimido-1-azetidineacetate, 1.24 g. of stannous chloride dihydrate and 50 ml. of dioxane was heated on a steam-bath for 1 hour. The solvent was evaporated, the residue dissolved in 50 ml. of chloroform, and the solution washed with 10 ml. of 1 N HCl, 25 ml. of water, 25 ml. of sat. NaHCO$_3$, 15 ml. of water, dried and evaporated to give 1.75 g. (74%) of crude product. The nmr spectrum showed the product to be a mixture of trans (5-epi) and cis penicillins in a ratio ca. 7:1 trans:cis. The neutral material was chromatographed on 28 g. of silica gel using 250 ml. of benzene and 500 ml. of a mixture of benzene-ethyl acetate (95:5) as eluting solvent. Fractions containing 20 ml. were collected in 17 minute intervals. Fractions 17–30, 1.38 g., contained 2,2,2-trichloroethyl 6-phthalimido-5-epi-penicillanate, $[\alpha]_D$−127.5°, (CHCl$_3$); nmr (CDCl$_3$) 96 (s, 3H) 105 (s, 3H), 242.5 (s, 1H), 291.5 (s, 2H), 329 (d, 1H, J = 2.0 Hz), 335 (d, 1H, J = 2.0 Hz), and 470 cps (m, 4 ArH); ir (CHCl) 1796 (β-lactam CO), 1764 and 1735 (phthalimido CO), and 1735 cm$^{-1}$ (ester CO).

In a similar experiment, cis penicillin was first isolated by dissolving the crude product in ethyl ether. The crystals, m.p. 235°–37°C., of 2,2,2-trichloroethyl 6-phthalimidopenicillanate were filtered, the filtrate evaporated and the crude ester of corresponding 5-epi-penicillin was purified by chromatography over silica gel.

EXAMPLE 3

A. Preparation of Benzhydryl 6-phthalimidopenicillanate

To a solution of 3.44 g. (0.01 mole) of 6-phthalimidopenicillanic acid in 30 ml. of ethyl acetate 2.33 g. (0.012 mole) of diphenyldiazomethane was added with stirring. After 20 minutes the purple color of unreacted diphenyldiazomethane was discharged with conc HCl and the solution washed with dilute $NaHCO_3$ and $H_2O$, dried, and evaporated to yield 4.42 g. of ester. This crystallized from a mixture of 30 ml. of ethanol and 15 ml. of acetone to give colorless silky needles, mp 161°–163°C.; $[\alpha]_D$+230.6° ($CHCl_3$); nmr ($CDCl_3$) 79 (s, 3H), 110 (s, 3H), 288 (s, H), 338 (d, 1H, J = 4 Hz), 343 (d, 1H, J = 4 Hz), 421 (s, 1H), 443 (m, 10 ArH), and 469 cps (m, 4 ArH); ir (CHCl) 1800 ($\beta$-lactam CO), 1785 and 1735 (phthalimido CO), 1750 $cm^{-1}$ (ester CO).

Anal. calc. for $C_{29}H_{24}N_2O_5S$: C, 67.95; H, 4.72; N, 5.47; S, 6.26; O, 15.61. Found: C, 68.14; H, 4.74; N, 5.55; S, 6.19; O. 15.47%.

B. Benzhydryl 2-chloro-α-(1'-chlorothio-1'-methylethyl)-4-oxo-3-phthalimido-1-azetidineacetate A solution of 17.5 g. of benzhydryl 6-phthalimidopenicillanate in 50 ml. of methylene chloride was cooled in an ice-bath and 34 ml. of 1M chlorine solution in carbon tetrachloride was added and stirred for 30 minutes. The solvent was evaporated and the residue dried in vacuo. The title compound was obtained almost in quantitative yield; nmr ($CDCl_3$) 100 (s, 3H), 104 (s, 3H), 288 (s, 1H), 328 (d, J = 1.5 Hz, 1H), 360 (d, J = 1.5 Hz, 1H), 422 (s, H), 443 (m, 10 ArH), and 469 cps (d, 4 ArH).

Anal. calc. for $C_{29}H_{24}Cl_2N_2O_5S$: C, 59.70; H, 4.15; cl, 12.15; N, 4.80; O, 13.71; S, 530. Found: C, 59.91; H, 4.28; Cl, 12.30; N, 4.59; O, 13.54; S, 5.50%.

C. Preparation of Benzhydryl 6-phthalimido-5-epi-penicillanate

A solution of 29.15 g. (0.05 mole) of benzhydryl 2-chloro-α-(1'-chlorothio-1'-methylethyl)-4-oxo-3-phthalimido-1-azetidineacetate and 9.5 g. (0.05 mole) of stannous chloride in 291 ml. of tetrahydrofuran was stirred at room temperature for 2 hours; the solvent was evaporated, the residue dissolved in ethyl acetate, washed twice with water, dried and the solvent evaporated to give a crude product which was chromatographed over silica gel using a linear gradient mixture of benzene-ethyl acetate. Fractions containing 20 ml. were collected at 17 minute intervals. Fractions 77–101, 6.0 g. of colorless solids, constituted benzhydryl 6-phthalimido-5-epi-penicillanate; $[\alpha]_D$–75° ($CHCl_3$); nmr ($CDCl_3$) 76 (s, 3H), 99 (s, 3H), 240 (s, 1H), 328 (d, 1H, J = 2.0 Hz), 335 (d, 1H, J = 2.0 Hz), 424 (s, 1H), 446 (m, 10 ArH), and 470 cps (m, 4 ArH); ir (CHCl) 1796 ($\beta$-lactam CO), 1785 and 1735 (phthalimido CO), and 1745 $cm^{-1}$ (ester CO).

Anal. Calc. for $C_{29}H_{24}N_2O_5S$: C, 67.95; H, 4.72; N, 5.47; S, 6.26; O, 15.61. Found: C, 68.03; H, 5.00; N, 5.38; S, 6.48; O, 15.82%.

EXAMPLE 4

Preparation of 6-Phthalimido-5-epi-penicillanic acid

A mixture of 620 mg. of benzhydryl 6-phthalimido-5-epi-penicillanate, 0.4 ml. of anisole and 1.6 ml. of trifluoroacetic acid was stirred in an ice-bath for 15 minutes, and then evaporated in vacuo. The residue was dissolved in ethyl acetate, the acid extracted with dilute $NaHCO_3$, the aqueous solution separated and acidified with conc Hcl, the desired acid re-extracted with ethyl acetate, the extract dried and evaporated. The title acid, 250 mg., was isolated as a colorless amorphous solid: $[\alpha]_d$–103.5° ($CHCl_3$); nmr ($CDCl_3$) 94 (s, 3H), 103 (s, 3H), 238.5 (s, 1H), 324.5 (d, 1H, J = 2.0 Hz), 330.5 (d, 1H, J = 2.0 Hz), and 472 cps (m, 4 ArH); ir (CHCl) 1795 ($\beta$-lactam CO), 1782 and 1735 $cm^{-1}$ (phthalimido CO).

Anal. Calc. for $C_{16}H_{14}N_2O_5S$: C, 55.48; H, 4.07; N, 8.09; O, 23.10; S, 9.26. Found: C, 55.29; H, 4.25; N, 7.97; O, 23.40; S, 9.47%.

EXAMPLE 5

The Reaction of trans methyl 2-chloro-α-(1'-chlorothio-1'-methylethyl)-4-oxo-3-phthalimido-1-azetidineacetate with acetic acid and zinc To a solution of 8.6 g. (0.02 mole) of trans methyl 2-chloro (1'-chlorothio-1'-methylethyl)-4-oxo-3-phthalimido-1-azetidineacetate in 50 ml. of toluene and 25 ml. of acetic acid, 3.6 g. of zinc dust was slowly added for 8 minutes. After stirring at room temperature for 1 hour, the solvent was evaporated, the residue dissolved in 100 ml. of ethyl acetate and 30 ml. of a saturated solution of sodium bicarbonate, the organic layer separated, washed with 30 ml. of water, dried ($Na_2SO_4$), and the solvent evaporated to give 8.15 g. of crude product. This was chromatographed over silica gel using a linear gradient mixture of benzene and ethylacetate. Fractions containing 21.5 ml. were collected at 20 minute intervals. Fractions 35–70, 1.3 g., were a mixture of four compounds; this material on recrystallization from 3 ml. of acetone afforded 290 mg. of colorless prisms of methyl 6-phthalimidopenicillanate, mp 171°–173°C.; nmr ($CDCl_3$) 9. (s, 3H), 110 (s, 3H), 228 (s, 3H), 281 (s, 1H), 334 (d, 1H, J = 4.0 Hz), 342 (d, 1H, J = 4.0 Hz), and 470 cps (m, 4 ArH).

The filtrate was evaporated and 200 mg. of the residue was chromatographed on a preparative thin layer chromatography silica gel plate using a mixture of cyclohexane and methyl ethyl ketone (4:1). The major stripe was extracted with chloroform and acetone giving 135 mg. of colorless product which was recrystalized from 2.5 ml. of a v/v mixture of cyclohexane and ketone (4:1) to give colorless rosettes, mp 174°–175°C., of methyl 6-phthalimido-5-epi-penicillanate; nmr ($CDCl_3$) 90 (s, 3H), 102 (s, 3H), 231 (s, 3H), 234.5 (s, 1H), 327 (d, 1H, J = 2.0 Hz), 334 (s, 1H, J = 2.0 Hz), and 471 cps (m, 4ArH). The mass spectrum showed a molecular ion at m/e 360.

Anal. calc. for $C_{17}H_{16}N_2O_5S$: C, 56.67; H, 4.47; N, 7.78; S, 8.90. Found: C, 56.42; H, 4.54; N, 7.92; S, 8.70%.

The remaining two compounds were identified as cis and trans isomers of methyl 2-acetoxy-α-(1'-mercapto- 2'-methylpropyl)-4-oxo-3-phthalimido-1-azetidineacetate.

Fractions 85–115, 2.83 g. of colorless amorphous solid, were a mixture of trans and cis (6:1) isomers of corresponding disulfides. The isomers were separated by using preparative thin layer chromatography silica plates: trans dimethyl 3,3'-dithiobis [3-methyl-2-(4'-acetoxy-3'-phthalimido-1'-azetidin-2'-onyl)butyrate] was an amorphous solid: nmr (CDCl$_3$) 100 (s, 12H), 128 (s, 6H), 230 (s, 6H), 274 (s, 2H), 317 (d, 2H, J = 1.5 Hz), 400 (d, 2H, J = 1.5 Hz) and 472 cps (m, ArH); ir (CHCl$_3$) 1800, 1789, 1757, and 1735 cm$^{-1}$.

Anal. calc. for $C_{38}H_{38}N_4O_{14}S_2$: C, 54.41; H, 4.57; N, 6.68; S, 7.65. Found: C, 54.25; H, 4.69; N, 6.38; S, 7.49%.

EXAMPLE 6

The reaction of transmethyl 2-chloro-α-(1'-chlorothio-1'-methylethyl)-4-oxo-3-phthalimido-1-azetidineacetate with sodium thiocyanate A solution of 4.31 g. (0.01 mole) of methyl 2-chloro-α-(1'-chlorothio-1'-methylethyl)-4-oxo-3-phthalimido-1-azetidineacetate in 50 ml. of benzene was mixed with a solution of 0.9 g. of sodium thiocyanate, the mixture stirred at room temperature for 15 minutes, washed with water, dried and the solvent evaporated. The residue was recrystallized from methylene chloride-petroleum ether, and colorless crystals of methyl 2-chloro-α-(1'-cyanodithia-1'-methylethyl)-4-oxo-3-phthalimido-1-azetidineacetate melted at 117°–119°C.; nmr (CDCl$_3$) 109 (s, 6H), 232 (s, 3H), 276 (s, 1H), 333 (d, 1H, J = 1.5 Hz), 364 (d, 1H, J = 1.5 Hz), and 472 cps (m, 4 ArH); ir (CHCl$_3$) 2155, 1800 (β-lactam CO), 1790, 1732 (phthalimido CO), and 1752 cm$^{-1}$ (ester CO).

Anal. calc. for $C_{18}H_{16}ClN_3O_5S_2$: C, 47.61; H, 3.55; Cl, 7.81; N, 9.26; S, 14.13. Found: C, 47.40; H, 3.56; Cl, 8.03; N, 9.43; S, 14.03%.

EXAMPLE 7

The reaction of methyl 2-chloro-α-(1'-cyanodithio-1-methylethyl)-4-oxo-3-phthalimido-1-azetidineacetate with acetic acid and zinc To a solution of 2.7 g. of methyl-2-chloro-α-(1'-cyanodithio-1'-methylethyl)-4-oxo-3-phthalimido-1-azetidineacetate in 40 ml. of acetic acid 2.7 g. of zinc dust was added in 10 minutes; the mixture was stirred at room temperature for 1 hour and filtered. The filtrate was evaporated, the residue dissolved in ethyl acetate, the solution washed with dilute NaHCO$_3$ and H$_2$O, dried, and evaporated to give 2.3 g. of a viscous oil. This was chromatographed over silica gel using a linear gradient mixture of benzene and ethyl acetate. Fractions containing 20 ml. were collected at 20 minute intervals. Fractions 31–81, 610 mg., contained a mixture of four products; after recrystallization from acetone 120 mg. of colorless prisms, mp 171°–173°C., of methyl 6-phthalimidopenicillanate were obtained. The filtrate was evaporated and the remaining three compounds were identified as: (a) methyl 6-phthalimido-5-epi-penicillanate, (b) cis and (c) trans methyl 2-acetoxy-α-(1'-mercapto-1'-methylethyl)-4-oxo-3-phthalimido-1-azetidineacetate.

Fractions 82–86 contained 17 mg. of colorless amorphous solid of trans dimethyl, 3,3'-dithiobis(3-methyl-2-(4'-acetoxy-3'-phthalimido-1'-azetidin-2-onyl)butyrate], nmr (CDCl$_3$) 100 (s, 12H), 128 (s, 6H), 230 (s, 6H), 274 (s, 2H), 317 (d, 2H, J = 1.5 Hz), 400 (d, 2H, J = 1.5 Hz), and 472 cps (m, 8 ArH).

Fractions 87–101, 640 mg., were a mixture of corresponding cis and trans disulfides.

EXAMPLE 8

Methyl 2-chloro-α-(1'-mercapto-1-methylethyl)-4-oxo-3-phthalimido-2-azetidineacetate Method A.

A mixture of 862 mg. (2 mM) of methyl 2-chloro-α-(1'-chlorothio-1'-methylethyl)-4-oxo-3-phthalimido-1-azetidineacetate, 25 ml. of carbon tetrachloride, 10 ml. of acetic acid, 374 mg. (2.2 mM) of potassium iodide and 40 ml. of a 0.1 N solution of sodium thiosulfate is stirred for 35 minutes at room temperature. The organic phase is separated and the aqueous phase is extracted with 35 ml. of carbon tetrachloride. The organic extracts are combined, and the resulting mixture is washed with water, dried and the solvent evaporated. The residue is then chromatographed over silica gel using a mixture of benzene and ethyl acetate (95:5) as the eluting solvent. Fractions 3 to 6 are combined, and 150 mg. of a colorless product is obtained by crystallization from 3.0 ml. of acetone with 1 ml. water. The title compound is obtained in the form of colorless needles, mp: 156°–157°C.; ir (KBr) 2578, 1780, 1770, 1742, and 1725 cm$^{-1}$; nmr (CHCl$_3$) 99 (s, 3H); 101 (s, 3H); 180 (s, 1H) exchanges with D$_2$O; 230 (s, 3H); 273 (s, 1H); 336.5 (d, 1H, J = 2 Hz), 387.5 (d, 1H, J = 2 Hz), 475 cps (m 4 ArH).

Anal. calc. for $C_{17}H_{16}ClN_2O_5S$: C, 51.58; H, 4.07; Cl, 8.96; N, 7.08; S, 8.10. Found: C, 51.35; H, 4.27; Cl, 9.14; N, 7.23; S, 7.98.

Method B.

A mixture of 4.31 g. (0.01 mole) of methyl 2-chloro-α-(1'-chlorothio-1-methylethyl)-4-oxo-3-phthalimido-2-azetidineacetate 2.36 g. (0.0105 mole) of stannous chloride dihydrate in 43 ml. of tetrahydrofuran was stirred at room temperature for 2 hours, and then evaporated to dryness on a rotavapor. The residue was dissolved in 43 ml. of ethyl acetate, washed with 20 ml. of water, a solution of NaHCO$_3$ (420 mg. in 20 ml. of water), and again 20 ml. of water, dried (MgSO$_4$), the solvent evaporated to give 3.55 g. (90%) of the title compound, which was crystallized from aqueous acetone. The colorless needles, mp 156°–57°C., are identical with the product obtained according to the Method A.

EXAMPLE 9

Preparation of Methyl 6-phthalimido-5-epi-penicillanate via mercapto compound

A mixture of 396 mg. of methyl 2-chloro-α-(1'-mercapto-1'-methylethyl)-4-oxo-3-phthalimido-2-azetidineacetate and 190 mg. of anhydrous stannous chloride in 10 ml. of tetrahydrofuran was heated on a steambath for 1 hour and the solvent evaporated. The residue was dissolved in 15 ml. of ethyl acetate, washed twice in 10 ml. of water, dried (MgSO$_4$), the solvent evaporated, and a crude product dried in vacuo. The nmr spectrum shows a complete conversion to the title compound. After recrystallization from methyl ethyl ketone and cyclohexane colorless prisms, mp. 174°–75°C., of methyl 6-phthalimido-5-epi-penicillanate were obtained.

EXAMPLE 10

Preparation of 2,2,2-Trichloroethyl 6-Succinimido-5-epi-penicillanate

A. Preparation of 2,2,2-trichloroethyl 6-($\beta$-carboxy)-propionamido penicillanate A mixture of 3.84 g. of the hydrochloride of 2,2,2-trichloroethyl 6-aminopenicillanate, 38 ml. of chloroform, 1.0 g. of succinic anhydride and 1.4 ml. of triethylamine is refluxed for 75 minutes, filtered and the filtrate washed with 10 ml. of 1 N solution of hydrochloric acid, twice with water and once with brine, dried and the solvent evaporated. Yield, 1.94 g.; nmr (CDCl$_3$) 96 (s, 3H), 103 (s, 3H), 160 (s, 4H), 275 (s, 1H), 290 (s, 2H), 339 (q, 1H J = 4 Hz), 346 (d, 1H J = 4 Hz) and 415 Hz (d, 1NH, J = 8 Hz).

B. Preparation of 2,2,2-trichloroethyl 6-succinimidopenicillanate

A mixture of 2.46 g. of 2,2,2-trichloroethyl 6-($\beta$-carboxy)propionamidopenicillanate, 40 ml. of methylene dichloride, 1.4 ml. of triethylamine and 0.5 ml. of ethyl chloroformate is stirred at 0°C. for 1 hour. After that it is washed with water and brine, the solvent evaporated to yield 1.59 g. of the crude product which is chromatographed over 30 g. of silica gel and eluted with benzene and ethyl acetate (90:10). Fractions 11–30 gave 430 mg. of 2,2,2-trichloroethyl 6-succinimidopenicillanate: ir (CHCl$_3$) 1801, 1775 and 1730 cm$^{-1}$; nmr (CDCl$_3$) 96 (s, 3H), 108 (s, 3H), 168 (s, 4H), 284 (s, 1H), 290 (d, J = 2 Hz, 2H), 330 (d, J = 4 Hz), and 336 Hz (d, J = 4 Hz, 1H).

C. 2,2,2-Trichloroethyl 2-chloro-α-(1'-chlorothio-1'-methylethyl)-4-oxo-3-succinimido-1-azetidineacetate A solution of 4.1 g. of 2,2,2-trichloroethyl 6-succinimido-penicillanate in 41 ml. of methylene chloride was cooled to −50°C. and 10 ml. of 1 M chlorine solution in carbon tetrachloride was added and stirred for 45 minutes. The solvent was evaporated and the residue dried on a pump. The title compound was obtained as a mixture of cis and trans isomers in a ratio of ca. 1:5.

D. 2,2,2-Trichloroethyl 6-succinimido-5-epi-penicillanate

A solution of 3.12 g. of 2,2,2-trichloroethyl 2-chloro-α-(1'-chlorothio-1'-methylethyl)-4-oxo-3-succinimido-1-azetidineacetate and 1.16 g. of anhydrous stannous chloride in 31 ml. of tetrahydrofurane was stirred at room temperature for 2 hours; the solvent evaporated, the residue dissolved in ethyl acetate, washed twice with water and once with brine, dried (MgSO$_4$) and the solvent evaporated to give 2.4 g. of a crude product which was chromatographed over 60 g. of silica gel using a linear gradient mixture of benzene ethyl acetate. Fractions containing 5-epi-penicillanate were collected and the solvent evaporated giving 700 mg. of pure product; nmr (CDCl$_3$) 94 (s, 3H), 103 (s, 3H), 164 (s, 4H), 239 (s, 1H), 291 (s, 2H), and 325 Hz (s, 2$\beta$-lactam H); ir (nujol) 1780, 1755 and 1710 cm$^{-1}$.

EXAMPLE 11

Preparation of 2,2,2-Trichloroethyl N-(3-phenyl-5-methyl-4-isoxazolyl) benzyl-5-eip-penicillanate A. 2,2,2-Trichloroethyl N-(3-phenyl-5-methyl-4-isoxazolyl)benzylpenicillanate A suspension of 2.36 g. of phosphorus pentachloride and 2.4 ml. of quinoline was cooled to −10°C. and 4.65 g. of 2,2,2-trichloroethyl benzylpenicillanate was added and stirred at −10°C. for 20 minutes. A solution was washed with 2.15 g. of sodium bicarbonate in 30 ml. of water, twice with 20 ml. of water and 20 ml. of brine, dried (MgSO$_4$), the solvent evaporated and the oily product dried in vacuo. The nmr spectrum shows the complete conversion to imido chloride. The oil was dissolved in 70 ml. of dioxane and 3.6 g. of potassium 3-phenyl-5-methylisoxazolyl-4-carboxylate was added and the mixture stirred at 40°C. for 4 hours. The solvent was evaporated, the residue dissolved in 50 ml. of chloroform and 25 ml. of water, the organic layer washed with a solution of sodium bicarbonate, water, 0.1N hydrochloric acid, water and brine. After drying the solvent was evaporated and 4.2 g. of a crude product chromatographed over 100 g. of silica gel using a mixture of benzene and ethyl acetate (95:5). Fractions (22 ml.) 41–91 gave 2.34 g. of 2,2,2-trichloroethyl N-(3-phenyl-5-methyl-4-isoxazolyl) benzylpenicillanate; nmr (CDCl$_3$) 90 (s, 3H), 101 (s, 3H), 152 (s, 3H), 229.5 (s, 2H), 275.5 (s, 1H), 285.5 (d, J = 1.5 Hz, 2H), 292 (d, J = 4.0 Hz, 1H), 318 (d, J = 4.0 Hz, 1H), 436.5 (m, 5H), and 448 Hz (s, 5H).

B. Chlorinolysis of bisacylimide ester

A solution of 1.3 g. of the acyclic imide obtained as described under A in 20 ml. of methylene chloride was cooled to −76°C. and 2.1 ml. of 1M chlorine solution in carbon tetrachloride was added and stirred for 30 minutes. The solvent was evaporated and the residue dried in vacuo. The crude 2,2,2-trichloroethyl 2-chloro-α-(1'-chlorothio-1'-methylethyl)-4-oxo-3-[N-(3-phenyl-5-methyl-4-isoxazolyl)-N-phenylacetyl]imido-1-azetidineacetate was immediately used in the next step.

C. Cyclization to 5-epi-penicillanate

The 2,2,2-trichloroethyl 2-chloro-α-(1'-chlorothio-1'-methylethyl)-4-oxo-3-[N-(3-phenyl-5-methyl-4-isoxazolyl)-N-phenylacetyl]imido-1-azetidineacetate obtained as described above under B was dissolved in 20 ml. of tetrahydrofurane and to a solution 390 mg. of anhydrous stannous chloride was added and stirred at room temperature for 2 hours. The solvent was evaporated, the residue dissolved in ethyl acetate and washed with water, dried and the solvent evaporated to give a crude product which was chromatographed over silica gel using benzene as eluting solvent. The desired 5-epi-penicillanate (title compound) was isolated and characterized by spectral data.

EXAMPLE 12

This example illustrates the use of the 5-epi-penicillanic acid compounds of this invention as an inhibitor of $\beta$-lactamase type enzymes. For this example the compound 6-phthalimido-5-epi-penicillanic acid was used.

The compound 6-phthalimido-5-epi-penicillanic acid was added to medium containing a cephalosporinase enzyme from contaminate bacterium. The reaction medium contained 11.4 millimole of cephalosporin C, 50 millimoles of [tris(hydroxymethyl)aminomethane] buffer pH 8.6, 0.2 ml. of the cephalosporinase enzyme, and either 5.78 millimoles or 2.89 millimoles of 6-phthalimido-5-epi-penicillanic acid. The total volume in each test was 2 ml. The reaction media were heated at 37°C. for 5 hours. Samples were taken at various times using 13 mm. discs. These discs were plated on agar seeded with Salmonella sp. The plates were incubated overnight at 38°C. Then the percent bioactivity of the cephalosporin C was measured. The results were as follows:

| Reaction | mM Inhibitor | Percent Bioactivity After 5 hours |
|---|---|---|
| Control (No inhibitor) | 0 | 0 |
| 6-phthalimido-5-epi penicillanic acid | 5.78 | 77 |
| 6-phthalimido-5-epi- penicillanic acid | 2.89 | 47 |

These results show that there was a substantial inhibition of cephalosporinase enzyme activity. These results show that the compound, 6-phthalimido-5-epi-penicillanic acid is useful as an enzyme inhibitor in fermentation media where cephalosporin C is being produced by fermentation methods.

EXAMPLE 13

Preparation of Methyl 6-phthalimido-5-epi-penicillanate via mercapto compound with zinc chloride A mixture of 396 mg. of methyl 2-chloro-α-(1-mercapto-1-methylethyl)-4-oxo-3-phthalimido-1-azetidineacetate and 136 mg. of zinc chloride in 10 ml. of tetrahydrofuran was heated on a steambath for 1 hour and the solvent evaporated. The residue was dissolved in 15 ml. of ethyl acetate, washed twice in 10 ml. of water, dried (MgSO$_4$), the solvent evaporated, and a crude product dried in vacuo. The nmr spectrum shows a complete conversion to the title compound. After recrystallization from methyl ethyl ketone and cyclohexane colorless prisms, mp. 174°–75°C., of methyl 6-phthalimido-5-epi-penicillanate were obtained.

I claim:
1. A compound of the formula

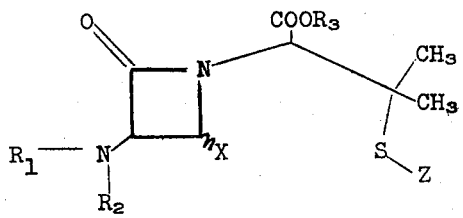

wherein R$_1$, taken alone, denotes an acyl group of the formula $$R_a—CH_2—CO$$

where R$_a$ is 

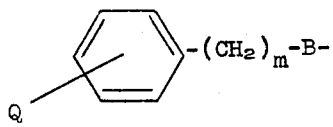

Q is hydrogen, chloro, bromo, C$_1$ to C$_3$-alkyl, C$_1$ to C$_3$-alkyloxy, nitro, or cyano; B is oxygen or a chemical bond; and m is an integer of from 0 to 2;

R$_2$, taken alone, is defined as R$_1$ above, or is

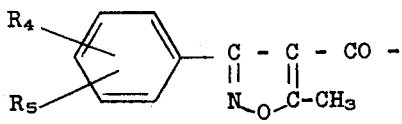

where each of R$_4$ and R$_5$ is hydrogen or a halogen (fluorine, chlorine, bromine, or iodine); or R$_1$ and R$_2$ taken together with the nitrogen to which they are bonded complete a cyclic imide radical derived from a hydrocarbon dibasic acid having from 3 to 20 carbon atoms, and R$_3$ is hydrogen, C$_1$ to C$_4$ alkyl, p-nitrobenzyl, p-methoxybenzyl, benzyl, benzyhydryl, phthalimidomethyl, succinimidomethyl, 2,2,2-trichloroethyl, trimethylsilyl, phenacyl, or p-halophenacyl in which halo denotes chlorine or bromine, X is chlorine or bromine and Z is hydrogen or —SCN.

2. A compound as defined in claim 1 wherein R$_1$ and R$_2$ are taken together with the nitrogen to which they are bonded to complete the succinimido or phthalimido group, R$_3$ is a C$_1$ to C$_4$-alkyl, p-nitrobenzyl, p-methoxybenzyl, benzyl, benzhydryl phthalimidomethyl, succinimidomethyl, 2,2,2-trichloroethyl, trimethylsilyl, phenacyl, or p-halophenacyl where halo denotes chlorine or bromine; X is chlorine, and Z is —SCN.

3. A compound as defined in claim 2 wherein the compound is methyl 2-chloro-α-(1'-cyanodithio-1'-methylethyl)-4-oxo-3-phthalimido-2-azetidineacetate.

4. A compound as defined in claim 1 wherein R$_1$ and R$_2$ are taken together with the nitrogen to which they are bonded to complete the succinimido or phthalimido group; R$_3$ is a C$_1$ to C$_4$-alkyl, p-nitrobenzyl, p-methoxybenzyl, benzyl, benzhydryl, phthalimidomethyl, succinimidomethyl, 2,2,2-trichloroethyl, trimethylsilyl, phenacyl, or p-halophenacyl where halo denotes chlorine or bromine; X is chlorine, and Z is hydrogen.

5. A compound as defined in claim 4 wherein the compound is methyl 2-chloro-α-(1'-mercapto-1'-methylethyl)-4-oxo-3-phthalimido-3-azetidineacetate.

* * * * *